(12) United States Patent
Olivier

(10) Patent No.: US 10,597,694 B2
(45) Date of Patent: Mar. 24, 2020

(54) SAMPLE PREPARATION DEVICE AND METHOD OF PREPARING A SAMPLE FOR STERILITY TESTING

(71) Applicant: Merck Patent GmbH, Darmstadt (DE)

(72) Inventor: Stephane Olivier, Rosheim (FR)

(73) Assignee: Merck Patent GmbH, Darmstadt (DE)

( * ) Notice: Subject to any disclaimer, the term of this patent is extended or adjusted under 35 U.S.C. 154(b) by 315 days.

(21) Appl. No.: 15/307,541

(22) PCT Filed: Mar. 31, 2015

(86) PCT No.: PCT/EP2015/000694
§ 371 (c)(1),
(2) Date: Oct. 28, 2016

(87) PCT Pub. No.: WO2015/165566
PCT Pub. Date: Nov. 5, 2015

(65) Prior Publication Data
US 2017/0051331 A1 Feb. 23, 2017

(30) Foreign Application Priority Data

Apr. 30, 2014 (EP) ..................................... 14290128

(51) Int. Cl.
*C12Q 1/22* (2006.01)
*G01N 1/40* (2006.01)
(Continued)

(52) U.S. Cl.
CPC ................ *C12Q 1/22* (2013.01); *B01L 3/502* (2013.01); *C12M 23/34* (2013.01); *C12M 23/38* (2013.01);
(Continued)

(58) Field of Classification Search
CPC .. C12Q 1/22; C12M 23/34; B01L 2400/0478; B01L 3/502; G01N 1/4077
See application file for complete search history.

(56) References Cited

U.S. PATENT DOCUMENTS 3,448,011 A 6/1969 Russomanno
4,036,698 A 7/1977 Bush et al.
(Continued)

FOREIGN PATENT DOCUMENTS

WO 2014/005669 A1 1/2014

OTHER PUBLICATIONS

International Search Report dated Aug. 21, 2015, issued in corresponding PCT/EP2015/000694, 3 pages.

*Primary Examiner* — Jill A Warden
*Assistant Examiner* — Dwayne K Handy
(74) *Attorney, Agent, or Firm* — Millen, White, Zelano and Branigan, P.C.

(57) ABSTRACT

A sample preparation device comprising a first chamber containing a first movable piston separating a first volume upstream and a second volume downstream the first piston, a second chamber containing a second movable piston separating a third volume upstream and a fourth volume downstream the second piston, and an inlet to the first volume and an outlet from the first volume. The first volume is connected with the third volume by a first communication path and the second volume is connected with the fourth volume by a second communication path.

15 Claims, 5 Drawing Sheets

(51) Int. Cl.
    *B01L 3/00*           (2006.01)
    *C12M 1/00*         (2006.01)
    *C12M 1/12*         (2006.01)
    *A61L 2/28*          (2006.01)

(52) U.S. Cl.
    CPC .......... *C12M 25/02* (2013.01); *G01N 1/4077* (2013.01); *A61L 2/28* (2013.01); *B01L 2200/0684* (2013.01); *B01L 2200/141* (2013.01); *B01L 2300/042* (2013.01); *B01L 2400/0457* (2013.01); *B01L 2400/0478* (2013.01); *G01N 2001/4088* (2013.01)

(56) References Cited

U.S. PATENT DOCUMENTS

| | | | |
|---|---|---|---|
| 6,349,850 B1 * | 2/2002 | Cheikh | ............ A61J 1/2089 141/100 |
| 2015/0153257 A1 | 6/2015 | Olivier et al. | |

* cited by examiner

SAMPLE PREPARATION DEVICE AND METHOD OF PREPARING A SAMPLE FOR STERILITY TESTING

The present invention concerns a sample preparation device, preferably for sterility and bio-burden testing, for example applicable for testing purposes in connection with the control of manufacturing processes or for final product testing in the pharmaceutical, biotech, food and beverage industries.

Sterility or bio-burden testing processes require a sample preparation method that involves specific consumables, hardware and sample preparation steps and the method is known as a standardized method throughout the industry. In the growth based sterility testing the sample preparation involves promoting the growth of any micro-organisms to be detected by a direct contact of liquid nutrition media that is introduced above a calibrated membrane filter that retains the micro-organisms and by incubating the container with the filter membrane and nutrition media at a predetermined temperature. Turbidity changes of the nutrition media indicate the presence of micro-organisms. Alternately, micro-organisms can be visually detected on the membrane filter.

The equipment and sample preparation steps of the sample preparation for such sterility and bio-burden testing includes the following typical steps:

1. Pre-Wetting

The pre-wetting is used to saturate the porosity of the membrane filter with the right rinsing buffer in order to avoid or reduce the risk of molecule binding to the membrane filter, mostly in case of antibiotic sterility testing. Such a process is described, for example, in European Pharmacopoeia 5.0, 2.6.1 Sterility.

A container with the buffer solution, i.e. a bottle, is connected to sample preparation devices (filtration containers) like the one described in U.S. Pat. No. 4,036,698 A, typically with a peristaltic pump located in a fluid connection between the buffer solution container and the sample preparation devices. The process requires to manually start and stop the peristaltic pump, to flip back and forth the buffer solution container and to unplug and plug vent closures on the sample preparation devices in a specific order. These steps are to be repeated on each of two or more sample preparation devices for each testing task.

2. Sample Filtration

This step is used to concentrate the micro-organisms on the surface of the membrane filter in the sample preparation devices. A container, i.e. a bottle or syringe, with a sample fluid is connected with the sample preparation devices via the peristaltic pump. The step requires to manually start and stop the peristaltic pump, to flip back and forth the sample container and to plug closures on the sample preparation devices in a specific order. These steps need to be performed simultaneously on each of the two or more sample preparation devices with a perfect equal splitting of the sample transfer and filtering through the respective sample preparation devices.

3. Rinsing

This step is used to rinse all tubing, the internal walls of the sample preparation device or container to ascertain that all the micro-organisms are collected at the surface of the membrane filter. In this step, the porosity of the membrane filter is rinsed in order to remove any inhibitor which may delay or prevent the growth development of potential contaminants (micro-organisms). This step, too, requires to connect a container, i.e. a bottle, with a rinsing fluid with the sample preparation devices via the peristaltic pump, and to manually start and stop the peristaltic pump, to flip back and forth the container with the rinsing fluid and to plug and unplug the respective vents on the sample preparation devices in a specific order to achieve the desired fluid flow through the volume of the devices. This step, too, has to be performed on each of the two or plural sample preparation devices.

4. Growth Media Addition

This step is used to bring the right volume of nutriments (aerobic or anaerobic) into each of the sample preparation devices above the membrane filter. A nutrition media container is connected to the sample preparation devices via the peristaltic pump. The step then requires to manually close the outlet of the sample preparation devices, start and stop the peristaltic pump, flip back and forth the nutrition media container, measure the right volume and keep the vent on the sample preparation device open and close it at the end of the step. This step is to be typically performed with one of the sample preparation devices with the aerobic media and then on another sample preparation device with the anaerobic media.

5. Incubation

In this step, the two or more sample preparation devices or containers are incubated under the specific incubation conditions for optimum growth development. The incubation is performed separately for the sample preparation devices or containers with the aerobic and anaerobic media.

6. Reading

Turbidity changes or local development of colonies on the filter membranes or filaments in the fluid are detected by regular reading, either by the naked eyes or by automated optical inspection technologies, to review and detect micro-bio-growth during the predetermined incubation term.

7. Identification

In case of a positive detection of a sample a liquid is extracted from the sample preparation device or container using a syringe or the like and further analysis is subsequently performed.

The above-mentioned steps are typical for sterility testing and a plurality of sample preparation devices have been developed for this process.

U.S. Pat. No. 4,036,698 A, for example, discloses a sample preparation method and apparatus for the testing of solutions such as antibiotic solutions to determine the presence of micro-organisms. The sample preparation device used in this method comprises a container formed as a cylinder of a transparent material. At one end of the container there are two ports, each provided with removable sealing caps. One of the ports includes a hydrophobic micro-porous membrane filter which is mechanically supported on its outer side by a support member and on the inner side by a similar support member. The filter performs the function of filtering all micro-organisms above a specific size from the flow through the filter. The porous support member is formed as a generally spiral grid allowing fluid to flow through while providing a general uniform mechanical support for the potentially fragile filter. The opposite end of the container is closed by a base member in which a further port is located and provided with a removable sealing cap. A membrane filter which is substantially the full diameter of the container is located at the junction between the cylinder wall of the container and the base member and it is sealed at its outer periphery to the wall of the container. The filter is a porous membrane.

Using this sample preparation device in the above-described process includes flowing the solution to be tested through the plastic container from the one end having the micro-porous membrane filter which strains micro-organisms beyond a certain size from the solution. The micro-organisms having passed are concentrated on the membrane filter at the opposite end of the container. Subsequently, the rinsing and culture or growth media are connected to the container to perform the steps in the order mentioned above.

A general disadvantage of the process is that the plural external containers or vials with culture or growth media and substances for generating the anaerobic atmosphere are to be connected and disconnected to the sample preparation devices or containers used in each testing task and a number of defined steps requiring large handling efforts are to be carried out in a predefined and precisely repeated routine.

It is the object of the present invention to provide a sample preparation device, preferably for sterility testing, and a method for preparing a sample for sterility testing using the device which is further improved with respect to the efficiency and accuracy of performing the steps of the process.

To solve the invention, the present invention provides a sample preparation device as defined in claim 1, a sample preparation set as defined in claim 14 and a method of preparing a sample for sterility testing as defined in claim 15. Preferred embodiments of the sample preparation device are defined in the dependent claims.

The sample preparation device, for example for use in the sterility testing process, comprises a first chamber containing a first movable piston separating a first volume upstream and a second volume downstream of the first piston, a second chamber containing a second movable piston separating a third volume upstream and a fourth volume downstream of the second piston/barrier, an inlet to the first volume and an outlet for the first volume. The first volume is connected with the third volume by a first fluid communication path and the second volume is connected with the fourth volume by a second communication path.

The first and second movable pistons are barriers for separating the respective volumes upstream and downstream (or above and below if a substantially vertical orientation of the device with a substantial horizontal orientation of the pistons is assumed) of the respective piston in the respective chambers before, while and after they are being moved in the respective chamber. The terms "upstream" and "downstream" are used to define the two sides of the pistons or volumes that they separate independent from the orientation of the device and these terms do not imply that a flow of fluid takes place through the pistons. In the description the term "piston/barrier" is used to refer to the structural and functional aspects of this element whereby it is understood that the structure ("piston") can be modified as long as the function ("movable barrier") is achieved.

Preferably, the first and/or second communication path(s) is/are adapted to be opened and closed by the movement of the first and second piston.

The sample preparation device of the invention is a closed system in which a first substance (i.e. a nutrition media) that is to be selectively introduced into a chamber containing another substance (i.e. the micro-organisms) and, optionally, a second substance (i.e. a gas generating agent) can be prepared in the respective chambers of the device and selectively mixed by communicating the various chambers by moving the pistons/barriers. Accordingly, the use of the sample preparation device of the invention, for example in a sterility testing process as described above, reduces the number of the steps for connecting/disconnecting external containers with such substances to/from the filtration container and thereby facilitates the performance of the number of steps, avoids contamination and improves repeatability of the process.

Although the invention is described with respect to the use of the sample preparation device in a sterility testing process, the device is useful in a more general sense for processes where certain substances provided in a volume are to be selectively transferred to another volume in a predictable, reliable, safe, sterile and repeatable manner.

In a preferred embodiment, the first volume contains a membrane support on which a membrane is placed or can be placed to separate the first volume into a cavity upstream and a cavity downstream of the membrane, wherein the inlet to the first volume communicates with one of the upstream and downstream cavities and the outlet communicates with the other one of the upstream and downstream cavities. The sample preparation device of this preferred embodiment is specifically suited for use in the sterility testing process as it includes or can include the micro-porous membrane filter that is used to collect the micro-organisms in the filtration step, following which, in a single process, the growth or nutrition media can be added and, optionally, the substance generating an aerobic atmosphere can be added to the chamber with the membrane by moving the pistons in the device.

In a preferred embodiment, the first piston is adapted to be actively moved in the first chamber, preferably by a force applied from the outside of the device, and the second piston is adapted to be passively moved in consequence of pressure changes induced in the second chamber by the movement of the first piston in the first chamber. This device is specifically advantageous in that it requires only a single manual activation of only one of the pistons in the device and the other piston is automatically translated within its chamber. This device further facilitates the handling of the sample preparation device and the carrying out of a process that requires the addition of one or more substances to a chamber containing a sample or filtered components of a sample to be tested.

The sample preparation device of the invention is compatible with existing sample preparation procedures including high pressure filtration and fluid supply using peristaltic pumps or a direct connection with a pressurized tank connected to the inlet, and vacuum filtration using a vacuum manifold or a liquid pump connected to the outlet of the device.

The method of preparing a sample for sterility testing according to the invention thus comprises providing at least one sample preparation device according to the invention and including a membrane in the first volume, pre-wetting the membrane, filtering the sample through the membrane, optionally rinsing the membrane, transferring the nutrition medium from the fourth volume into the second volume by moving the first and second piston, thereby bringing the nutrition medium in contact with the membrane, incubating the sample preparation device in specific incubation conditions, and inspecting the membrane for the existence of micro-organisms and/or extracting micro-organisms from the sample preparation device.

BRIEF DESCRIPTION OF DRAWINGS

The present invention will now be described on the basis of a number of preferred embodiments using the attached drawing. In this drawing.

The sample preparation device of the invention and the method of preparing a sample for sterility testing using the sample preparation device will now be described below referring to the schematic principle of the device and to various specific embodiments of the principle.

Figure 1:
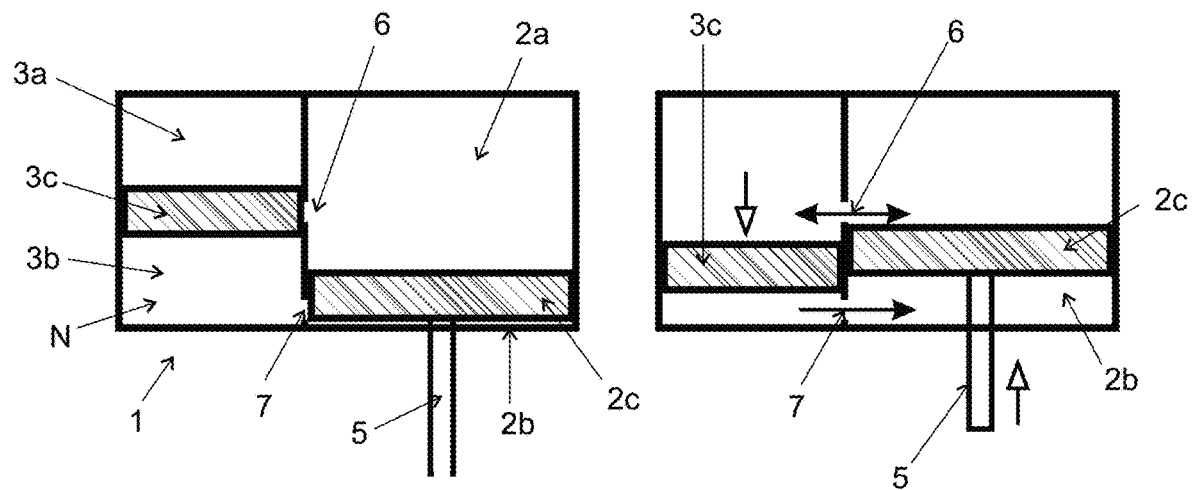
FIG. 1 shows a schematic representation of a sample preparation device of the present invention to explain the functional principle.

FIG. 1 shows the sample preparation device 1 with its basic structural elements. The sample preparation device 1 comprises a first chamber 2 containing a first movable piston/barrier 2c separating a first volume 2a above (upstream) and a second volume 2b below (downstream) the first piston/barrier 2c. A second chamber 3 contains a second movable piston/barrier 3c separating a third volume 3a above (upstream) and a fourth volume 3b below (downstream) the second piston/barrier 3c. An inlet (not shown in the FIG. 1) to the first volume 2a and an outlet 5 from the first volume 2a are provided. The first volume 2a is connected with the third volume 3a by a first fluid communication path 6 and the second volume 2b is connected with the fourth volume 3b by a second communication path 7. The first and second pistons/barriers 2c, 3c are located, in a starting position, such that they close the first and second communication paths 6, 7 (shown on the left side of FIG. 1).

Moving of the pistons from the starting position into an operative position (for example shown on the right side in FIG. 1) in the respective chambers selectively opens the first and/or second communication paths 6, 7 and establishes a fluid connection between the first volume 2a and the third volume 3a through the first communication path 6 and between the second volume 2b and the fourth volume 3b through the second communication path 7. Before the first piston 2c is moved into its operating position the inlet (not shown) and the outlet 5 are closed. The outlet 5 is preferably closed before the piston 2c is moved. The inlet (not shown) is closed before the piston is moved if it is through a port that is manually opened/closed. The inlet can be automatically closed by the first piston when the first piston is moved a certain distance from its starting position. Moving the pistons back to their starting positions can again close the communication paths and separate the volumes from each other although a single, i.e. one-way opening might be sufficient for the desired process.

The device shown in FIG. 1 can be preferably used for the sterility testing process as described in the introduction. The fourth volume 3b of the second chamber in this case can be pre-filled with a growth or nutrition media and the second volume 3a of the second chamber can be pre-filled with an anaerobic generation substance. Such an anaerobic generation substance is known per se in the form of gas-generating sachets consisting of a reagent sachet containing inorganic carbonate, activated carbon, ascorbic acid and water or other ingredients needed to create a specific atmosphere for specimen incubation. The substance becomes activated by exposure to air and the substance rapidly reduces the oxygen concentration within the respective volume. At the same time, inorganic carbonate produces carbon dioxide and this produces the atmosphere suitable to support the primary isolation and cultivation of anaerobic, micro-aerophilic or capnophilic bacteria by use of gas-generating substances of the respective type inside the third volume of the second chamber. The exposure to air is made and the substance is activated when the second piston/barrier opens the first communication path 6 by moving downward within the second chamber as shown on the right side of FIG. 1.

The first piston/barrier 2c is adapted to be actively moved in the first chamber 2, preferably by a force applied from the outside of the device 1 through a rod 13 of the piston extending to the outside of the device. This movement is shown in principle on the right side of FIG. 1. The second piston/barrier 3c is adapted to be passively moved in consequence of the pressure changes induced in the second chamber 3 by the movement of the first piston/barrier 2c in the first chamber 2. This passive movement is achieved in that the third volume contains a gas that can expand due to gas dilatation properties. The fourth volume 3b contains typically a liquid that can be considered as non-expansible. Due to the gas expansion in the third volume 3a and the presence of liquid in the fourth volume 3b, and due to the minimized first volume 2b in the initial position, the actuation of the first piston/barrier 2c in the first chamber 2 induces a translation of the second piston/barrier 3c in the second chamber 3. The translation of the first piston 2c in the first chamber 2 opens the second communication path 7 at or below the first piston and allows a liquid transfer from the fourth volume 3b to the second volume 2b. The resulting induced movement of the second piston opens the first communication path 6 between the first volume and the third volume allowing gas exchange and, if provided, generating an anaerobic environment by activating the anaerobic generation substance, for example a gas-generating powder or sachet, in the third volume based on the activation principle described above.

Figure 2:
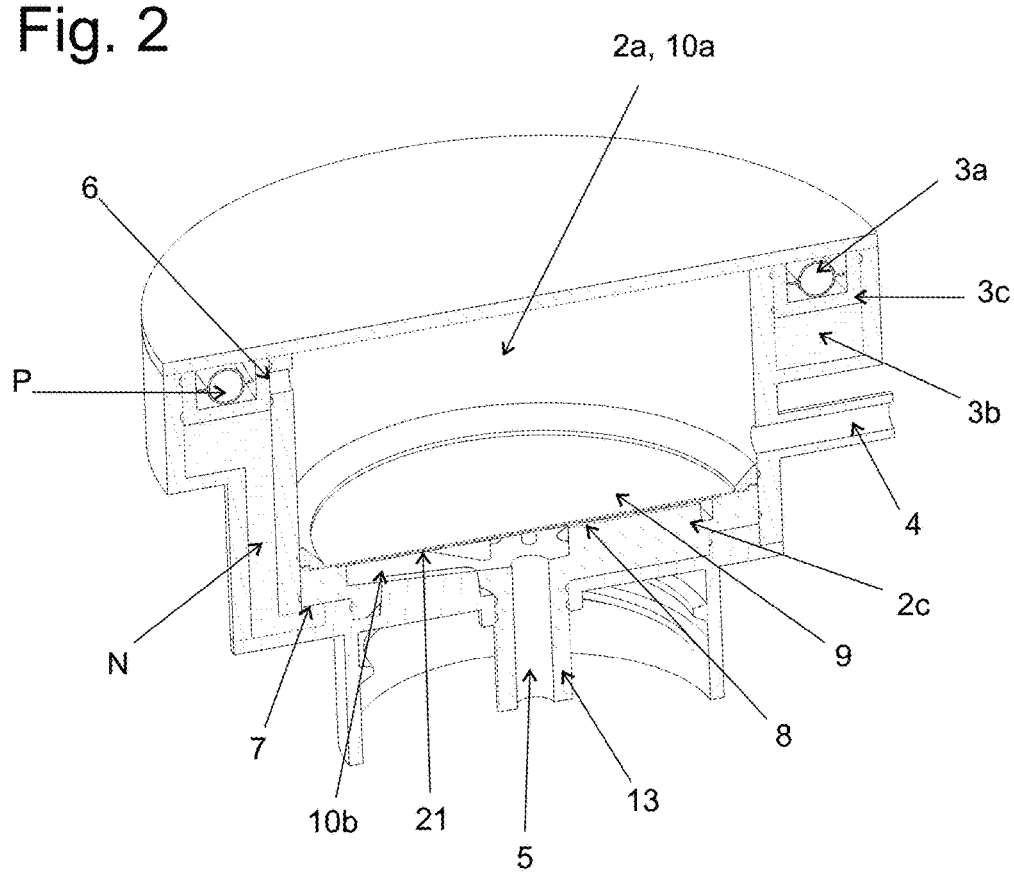
FIG. 2 shows a cross section perspective view of a preferred embodiment of the sample preparation device using the principle shown in FIG. 1.

The FIG. 2 shows a practical embodiment of the sample preparation device of the invention, the principle of which is explained on the basis of FIG. 1, wherein the first and second chambers 2, 3 are integrated in a substantially concentric arrangement with the second chamber surrounding the periphery of the first chamber. The same reference numerals are used to identify the functional elements of the sample preparation device. The second volume of the first chamber is not shown in this drawing as it is occupied by the first piston 2c. The FIG. 2 shows the sample preparation device in the starting position. The first volume 2a contains a membrane support 8 on an upper part of the first piston 2c, on which membrane support 8 a preferably micro-porous membrane 9 is placed or can be placed to separate the first volume 2a into a cavity 10a upstream of the membrane 9 and a cavity 10b downstream of the membrane 9. An inlet 4 (omitted in FIG. 1) to the first volume 2a is formed in a peripheral wall of the inner or first chamber and communicates the outside with the upstream cavity 10a in the first volume 2a of the first chamber. An outlet 5 communicates the outside with the downstream cavity 10b in the first volume 2a of the first chamber. In this example, the outlet 5 extends through a rod 13 of the first piston 2c.

A growth or nutrition media N is provided in the device in the fourth volume 3b of the second chamber. An anaerobic generation substance P (in the form of powder or pellets or a sachet) is optionally provided in the device in the third volume 3a of the second chamber.

Figure 3A:
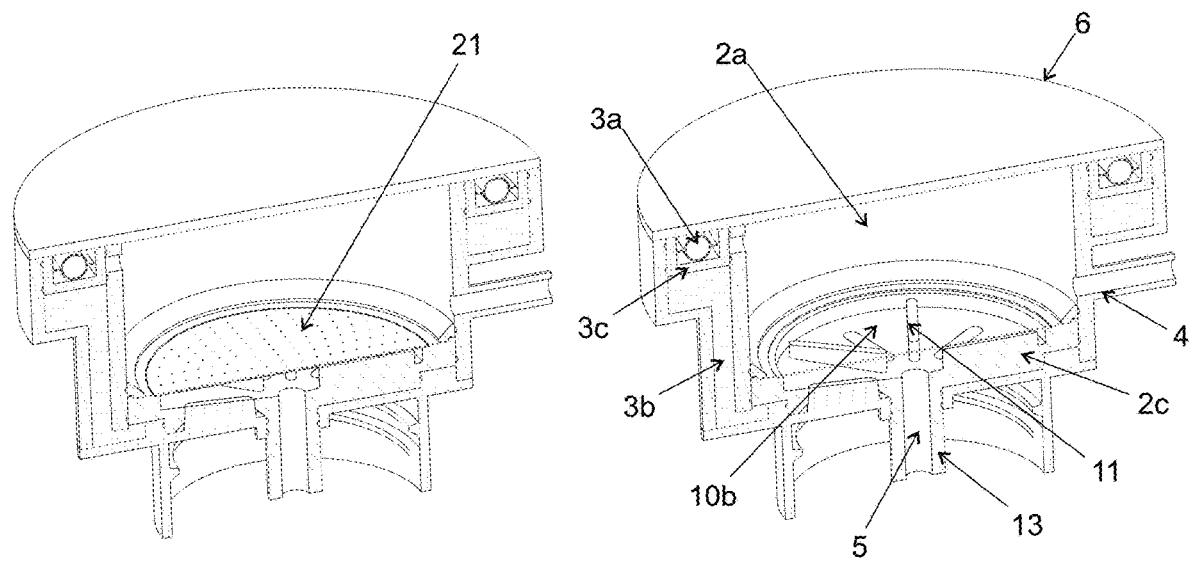
FIGS. 3A and B show details of the sample preparation device of FIG. 2 in operation.
Figure 3B:
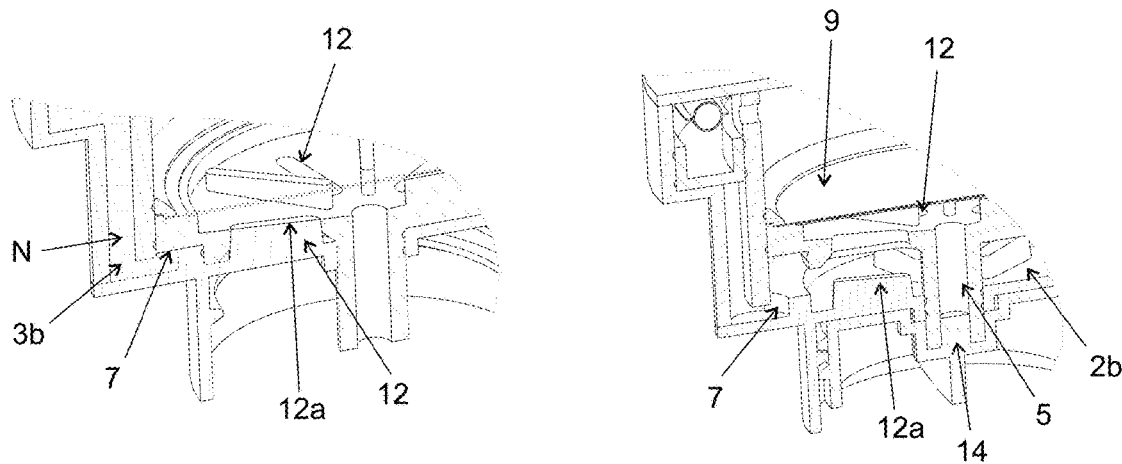

As shown in FIG. 3A, the cavity 10b downstream of the membrane is formed by a support structure 11 on the first piston/barrier 2c which preferably comprises an arrangement of ribs and/or channels formed in the axial face of the first piston/barrier 2c. As shown in FIG. 3B, the first piston/barrier 2c also contains one or more communication openings 12 communicating the first volume 2a, preferably the cavity 10b downstream of the membrane 9, if provided, with the second volume 2b. These communication openings 12 are closed when the first piston/barrier 2c is in the starting position (shown in FIGS. 3A and 3B, left side) and they are opened when the first piston/barrier 2c is moved away from the starting position towards the operating position (shown in FIG. 3B, right side). This is achieved in that the bottom of the second volume in the first chamber contains complementary mating protrusions 12a received in the communication openings 12 to close these openings 12 when the first piston 2c is in the lowest or starting position. Moving of the first piston in the first chamber not only opens the communication openings 12 but also opens the second communication path 7 between the fourth volume 3b and the second volume 2b of the first chamber formed below the first piston as shown in FIG. 3B.

Using the sample preparation device of FIGS. 2 and 3 in the sterility testing process described above includes rinsing of the membrane 9 on the membrane support through the inlet 4 and the outlet 5 while the first and second pistons are in the starting position as shown in FIG. 3A. In the second step, the sample fluid is transferred to the first volume 2a through the inlet 4 and outlet 5 to filter the sample to concentrate the micro-organisms on the surface of the membrane 9. Thereafter, the rinsing step is performed, again through the inlet 4 and the outlet 5 like in the prior art while the first and second pistons are still in the starting position.

Following that the steps of adding the growth or nutrition media and (optionally) the generation of the anaerobic atmosphere are performed in a single action in that the first piston is actively moved from the starting position shown in FIG. 3A to the operative position shown in FIG. 3B, right side. This movement transfers the growth or nutrition media from the fourth volume 3b in the second chamber 3 through the communication path 7 to the second volume 2b in the first chamber and further to the cavity 10b below the membrane 9 through the communication openings 12 in the piston. In the operative position the inlet 4 is preferably closed by the first piston/barrier 2c. The movement of the first piston in the first chamber induces the movement of the second piston 3c in the second chamber and this movement opens the first communication path 6 between the first volume 2a and the third volume 3a. The communication established between the first volume that will serve as the incubation chamber above the membrane and the anaerobic generation substance in the third volume activates the substance to produce the specific atmosphere for specimen incubation. The first communication path 6 allows the specific atmosphere to extend into the first volume 2a or incubation chamber above the membrane 9 and get in contact with the specimens on the membrane. The membrane 9 in the first volume can be supported by a mesh structure 21 provided on the upper surface of the first piston to limit the membrane deformation and avoid local stress which could damage the membrane and allow filtered sample to be drained to the outlet 5 (outlet port). The mesh structure 21 is visible in FIG. 3A, left side after the membrane 9 has been removed for illustrative purposes.

The active moving of the first piston in the first chamber is effected by a cooperation of the first piston/barrier 2c with a separate movable cap member 14 attached or attachable to the device 1 so as to be able to transfer a force applied from the outside to the cap member 14 onto the first piston/barrier 2c to move the first piston/barrier 2c and to selectively/simultaneously close the outlet port 5 from the first volume 2a that preferably extends through the moving rod 13 and a part of the first piston/barrier 2c. The principle is explained by reference to FIG. 4 which shows the steps of attaching the cap member 14 to the device (1), flipping the device upside down (2) and moving the first piston in the first chamber by twisting the cap member (3), thereby rotating and axially moving the cap member 14 by way of a threaded engagement between the cap member and a receptacle in the device.

To move the piston from the starting position to the operative position the cap member 14 is screwed into a mating receptacle in the device 1. Simultaneously therewith, the outlet port 5 is closed by a mating sealing feature 14a on the cap member 14. The cap member 14 has a handle 14b or other feature supporting the grip of the hand of a user or of a tool to twist the cap member in the receptacle. Since the membrane can be considered as "airtight" due to the membrane bubble point (e.g. the necessary air pressure needed to remove the liquid held by capillarity in the membrane porosity), the required pressure to pass the bubble point is greater than 1 bar for the micro-porous membrane typically used in the sterility testing processes.

By moving the piston to the operative position as described above, the growth or nutrition media N is transferred from the fourth volume to the second volume and to the cavity 10b under the membrane. This operation can be performed in a top-down position to allow the media to fall down in contact with the membrane by gravity and to collect air bubbles at the top of the second volume. As described above the active moving of the first piston in the first chamber induces the passive movement of the second piston and the translation of the second piston opens the communication path between the incubation chamber and the third volume containing (optionally) the anaerobic generation substance.

Figure 4:
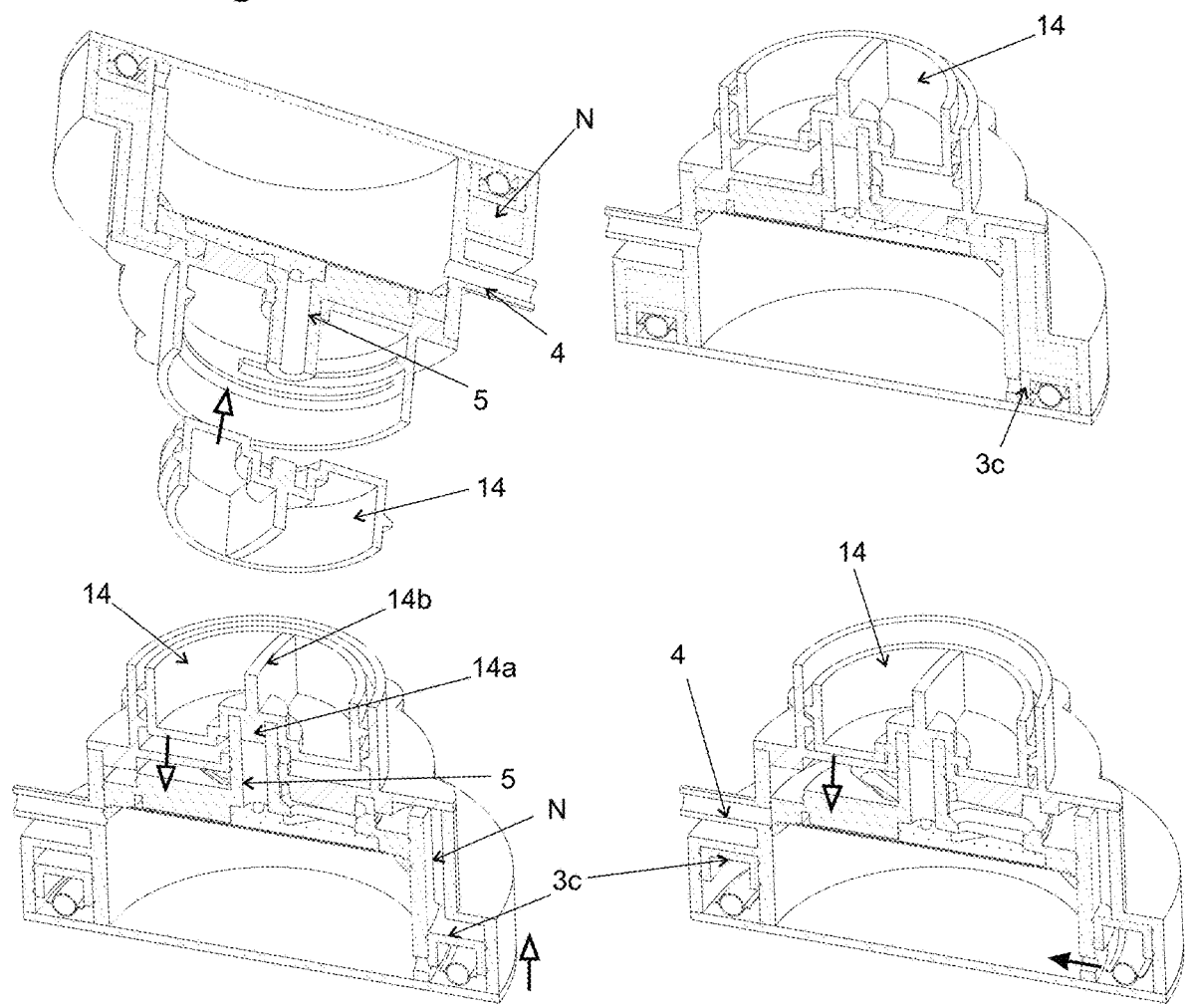
FIG. 4 shows the sample preparation device of FIG. 2 with respect to other details of its operation.

Preferably, the cap member 14 is automatically locked in its final position (see FIG. 4, (4)) and, if desired for security purposes, in a manner that it cannot be removed (i.e. by providing a locking engagement). In this position the first piston closes the inlet 4 to the first volume incubation chamber and any external tubing connected to the inlet port can be removed.

Figure 5:
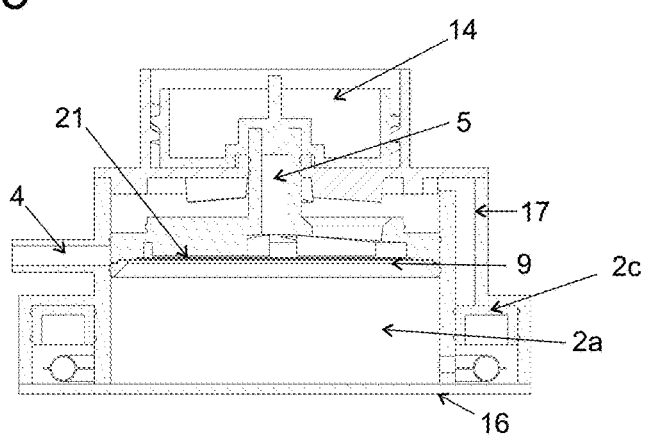
FIG. 5 shows a modification of the sample preparation device of FIG. 2 with certain viewing windows in a reading step of a sample preparation process.

Subsequently, the sample preparation device can be subjected to the further handling including incubation of the devices according to the aerobic or anaerobic development in different temperature environments and the typical reading and/or identification steps. FIG. 5 shows a modification of the sample preparation device of FIG. 2 with certain transparent viewing windows 16,17 in the side of the chamber opposite the membrane to allow viewing of the incubation volume or membrane of the first chamber, and in a peripheral wall(s) surrounding the growth or nutrition media and optionally the volume holding the anaerobic generation substance which is advantageous to allow inspection of the transfer step of the media/substance and allows the reading and detection of the micro-organism growth in the reading step of a sample preparation process.

Figure 6:
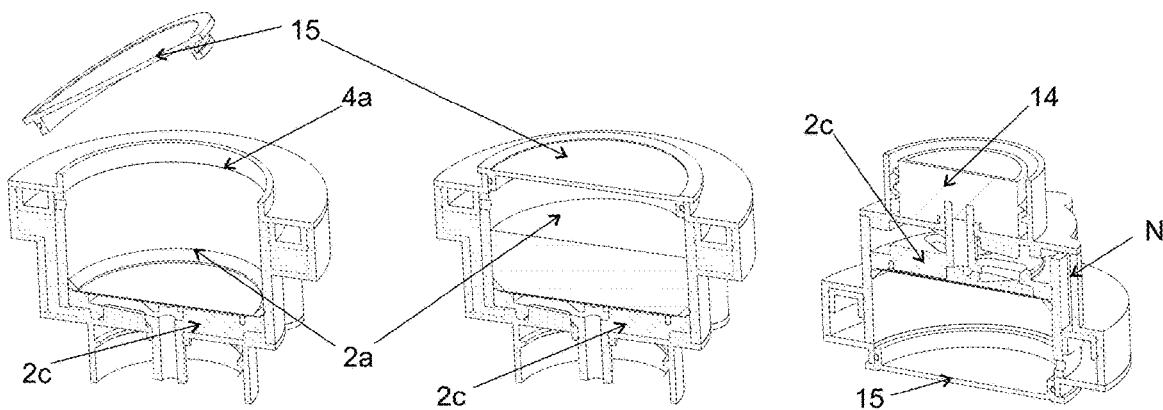
FIG. 6 shows a modification of the sample preparation device of FIG. 2 with a removable lid.

FIG. 6 shows a variation of the embodiment of the sample preparation device of the invention which has, instead of an inlet 4 in the form of a port adapted to be connected to external tubing (or in addition to such port), a lid 15 removably attached to the first chamber 2, wherein the lid 15 is preferably transparent to allow inspection of the incubation volume or membrane of the first chamber, either by the naked eye or by using optical automatic detection devices. The removable lid 15 also allows addition of rinsing and/or sample fluids to the first volume 2*a* of the device through the open top 4*a* of the first chamber serving as the inlet and this Figure shows the sequence of steps of filling the sample fluid into the device, filtering the sample through the outlet 5 and closing the outlet by means of the plug as described above, which automatically initiates the transfer of the nutrition media to the incubation chamber as described above.

Although not shown in the drawing the sample preparation device of the embodiment having the inlet port 4 can be used in an inline testing arrangement directly and, if necessary, permanently connected to sampling ports of laboratory equipment.

Figure 7:
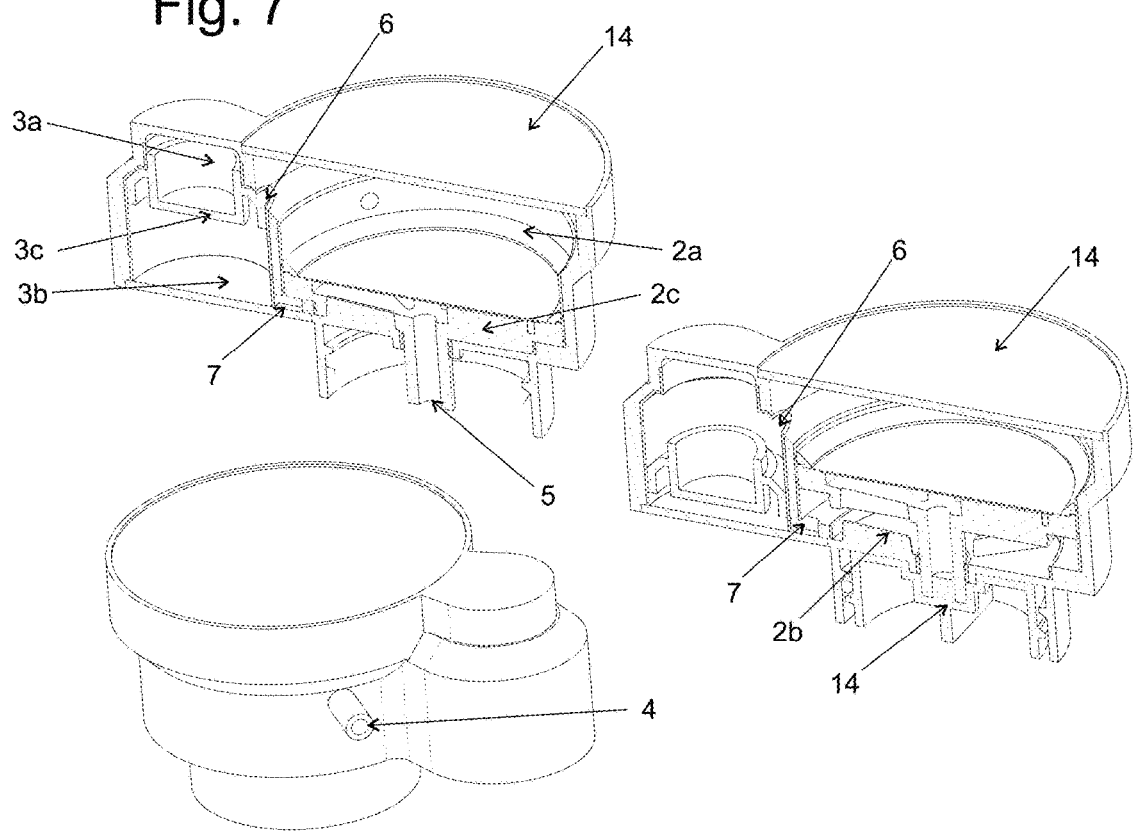
FIG. 7 shows a cross section side view and a perspective view of a further embodiment of the sample preparation device of the invention using the principle shown in FIG. 1 with a modified arrangement of the chambers.

The FIG. 7 shows a further embodiment where the first and second chambers are not concentrically arranged as in FIG. 2 but are laterally arranged but nevertheless integrally connected in the device. The embodiment of FIG. 7 also has the transparent removable lid closing the first volume or incubation volume 2*a*. The second chamber can be integrated with the first chamber but can also be removably attached therewith. This allows easy and modular manufacturing of the sample preparation device in that the second chamber including the desired nutrition media and, optionally, the anaerobic generation substance is selectively attached to the first chamber. This concept reduces the number of components necessary to produce sample preparation devices for different testing applications. The connection of the first chamber and of the second chamber needs to establish communication of the first and second communication paths between the respective volumes.

Figure 8:
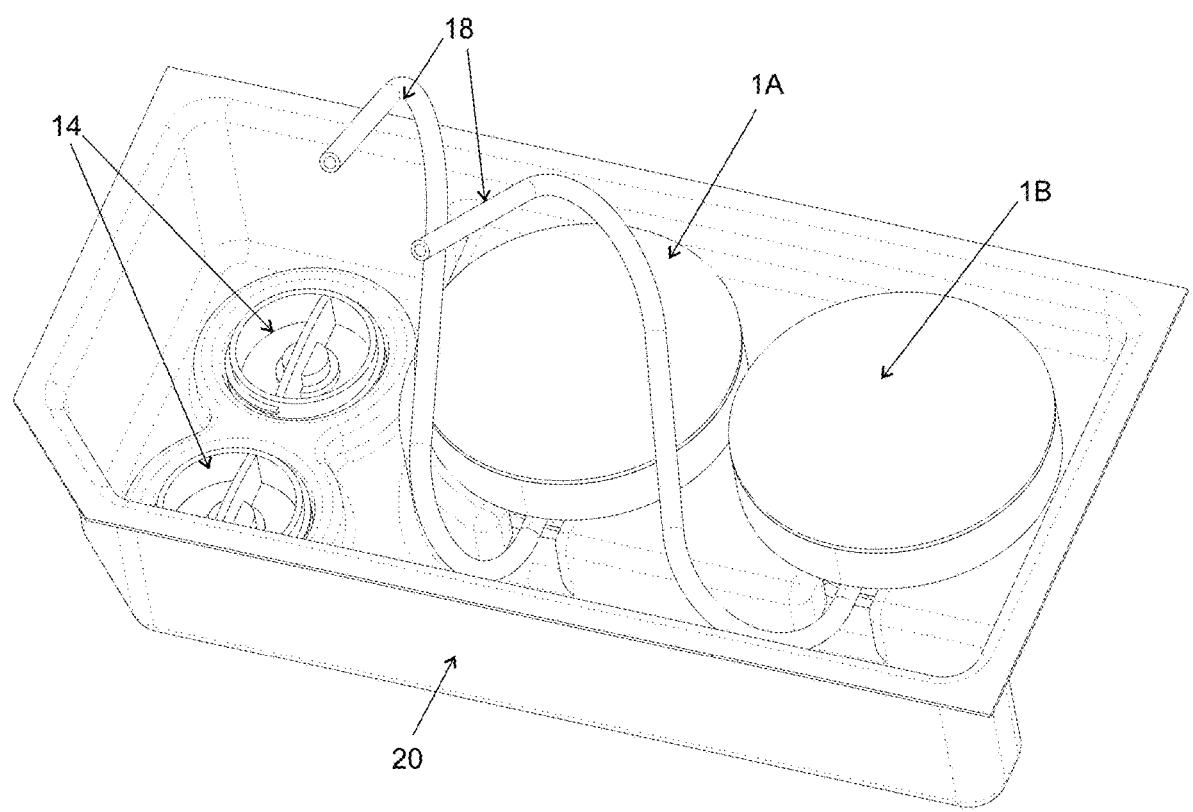
FIG. 8 shows a sample preparation set including two sample preparation devices of the type shown in FIG. 2.

The FIG. 8 shows an example of a sample preparation set comprising two sample preparation devices 1A, 1B of the type shown in FIG. 2/3 and a tubing set 18 designed to connect the inlets of the sample preparation devices with a common vented needle or sampling port (not shown in the drawing) for distributing a fluid to the sample preparation devices in precise aliquots. The two sample preparation devices in the set include one for anaerobic conditions 1A and including consequently the anaerobic generation substance in the third volume while the other one 1B is for aerobic conditions and consequently does not include the anaerobic generation substance. The tubing set 18 can be designed for the respective application and there could be more than two of the sample preparation devices depending on the need. The sample preparation devices could be loaded with the same or with different nutrition media in the fourth volume. The caps 14 used to plug the outlet and move the first piston in the first chamber as described are also pre-arranged in a packaging 20 of the set. Further functional elements of a testing equipment including tubing, claims, needles, etc., can be included in the set. The entire package can be in a sterilized blister to avoid contamination of pre-sterilized content.

The use of the set and the introduction of the rinsing or sample fluids through the inlet port and out from the outlet port can be performed as described in connection with the prior art by using external pumps like peristaltic pumps, pressurized tanks or syringes at the inlet or vacuum devices at the outlet. The incubation also can be performed as in the prior art and the circumstances depend on the germs or bacteria to be detected because they have different and specific growth conditions. Likewise, the growth or nutriment media provided in the sample preparation device are specific to the panel of germs or bacteria to be detected and to the environmental conditions and incubation temperature conditions. Since some micro-organisms require aerobic environments while others require anaerobic conditions to grow, the two different sample preparation devices are provided, one having the anaerobic generation powder or sachet provided in the third volume of the second chamber and one having no such substance, e.g. having an empty third volume containing atmospheric gas with oxygen.

The sample preparation device of the invention provides the following advantages, especially in connection with a method of preparing a sample for sterility testing. The system is completely closed during all the sample preparation steps comprising the addition of growth media and, optionally, of anaerobic generation substance. The sample preparation reliability and repeatability is improved in that the growth media addition is performed in a single step instead of in complex multistep protocols. The device allows the correct volumes to be transferred and it excludes mistakes or confusion with respect to the association between nutrition media and anaerobic generating substance. Errors and hazards due to inadvertent omission of closing of the inlet and outlet is avoided because the inlet is automatically closed when the piston is moved to the operative position whereas the outlet is closed once the cap member used to actively transfer the first piston to the operative position is attached to the device.

At the same time, the sample preparation device of the invention is compatible with laboratory equipment including pumps, pressurized tanks or vacuum systems for performing the preparatory steps of rinsing and sample filtration. It is also compatible with current incubation and identification protocols. Lastly, the sample preparation device facilitates the handling of waste as it reduces the number of separate and independent containers used in the entire sterility testing process.

The invention claimed is:

1. A sample preparation device (1) comprising
a first chamber (2) containing a first movable piston (2C), moved by a force from outside the device, through a rod of the first piston extending to the outside of the device, said first movable piston separating a first volume (2A) upstream of the first movable piston and a second volume (2B) downstream of the first movable piston (2C);
a second chamber (3) containing a second movable piston (3C) adapted to be passively moved in consequence of pressure changes induced in the second chamber by the movement of the first piston in the first chamber separating a third volume (3A) upstream of the second movable piston and a fourth volume (3B) downstream of the second movable piston (3C);
an inlet (4;4A) to the first volume (2A) and an outlet (5) from the first volume (2A);
wherein the first volume (2A) is connected with the third volume (3A) by a first communication path (6) and the second volume (2B) is connected with the fourth volume (3B) by a second communication path (7).

2. The sample preparation device (1) according to claim 1, wherein the first and/or second communication path (6,7)

is/are adapted to be opened and/or closed by a movement of the first and second piston (2C,3C).

3. The sample preparation device (1) according to claim 2, wherein the first communication path (6) is closed by the second piston (3C) in a starting position and is adapted to be opened by a movement of the second piston (3C) into an operative position, and the second communication path (7) is closed by the first piston (2C) in a starting position and is adapted to be opened by a movement of the first piston (2C) into an operative position.

4. The sample preparation device (1) according to claim 1, wherein the first volume (2A) contains a membrane support (8) on which a membrane (9) is placed or can be placed to separate the first volume (2A) into a cavity (10A) upstream of the membrane and a cavity (10B) downstream of the membrane (9), the inlet (4;4A) to the first volume (2A) communicating with one of the upstream and downstream cavities (10A,10B) and the outlet (5) communicating with the other one of the upstream and downstream cavities (10A,10B).

5. The sample preparation device (1) according to claim 4, wherein one of the cavities (10A,10B) is formed by a support structure (11) on the first piston (2C) for the membrane (9), said support structure (11) preferably comprises an arrangement of ribs and/or channels formed in the first piston (2C).

6. The sample preparation device (1) according to claim 1, wherein the first piston (2C) contains one or more communication openings (12) communicating the first volume (2A), preferably the cavity (10B) downstream of the membrane (9) if provided, with the second volume (2B), wherein the communication openings (12) are closed when the first piston (2C) is in a/the starting position and are opened when the first piston (2C) is moved towards a/the operative position.

7. The sample preparation device (1) according to claim 1, wherein the inlet (4) is adapted to be closed by the first piston (2C) in one of its moving positions within the first chamber (2), preferably in an operating position.

8. The sample preparation device (1) according to claim 1, wherein
the first piston (2C) is adapted to be actively moved in the first chamber (2), by a force applied from outside the device, through the rod of the first piston extending to the outside of the device (1), and
the second piston (3C) is adapted to be passively moved in consequence of pressure changes induced in the second chamber (3) by the movement of the first piston (2C) in the first chamber (2).

9. The sample preparation device (1) according to claim 1, wherein one of the inlet (4) and outlet (5) to/from the first volume (2A) extends through a part of the first piston (2C), preferably through a moving rod (13) thereof.

10. The sample preparation device (1) according to claim 9, wherein the first piston (2C) is arranged to cooperate with a cap (14) attached or attachable to the device (1) so as to be able to transfer a force applied from the outside onto the first piston (2C) to move the first piston (2C) and to selectively/simultaneously close the one of the inlet (4) and outlet (5).

11. The sample preparation device (1) according to claim 9, wherein the cap (14) is supported on the device (1) so as to be rotatable and/or axially movable.

12. The sample preparation device (1) according to claim 1, wherein one of the inlet (4A) and outlet (5) to/from the first volume (2A) is in the form of a lid (15) removably attached to an opening of the first chamber (2), wherein the lid (15) is preferably transparent to allow inspection of a/the membrane (9) in the first volume (2A) of the first chamber (2).

13. The sample preparation device (1) according to claim 1, wherein
the fourth volume (3B) is pre-filled with a nutrition medium; and
the third volume (3A) is optionally pre-filled with an anaerobic generation substance.

14. A sample preparation set comprising:
two or more sample preparation devices (1) according to claim 1, and
a tubing set (18) designed to connect the inlets of the sample preparation devices (1) with a common connector for distributing a fluid to the sample preparation devices (1).

15. A method of preparing a sample for sterility testing, comprising:
providing at least one sample preparation device (1) according to claim 13 and including a membrane (9) in the first volume (2A);
pre-wetting the membrane (9);
filtering the sample through the membrane (9);
optionally rinsing the membrane (9);
transferring the nutrition medium from the fourth volume (3B) into the second volume (2B) by moving the first and second piston (2C,3C), thereby bringing the nutrition medium in contact with the membrane (9);
incubating the sample preparation device (1) in specific incubation conditions; and
inspecting the membrane (9) for the existence of micro-organisms and/or extracting micro-organisms from the sample preparation device (1).

* * * * *